United States Patent
O'Shaughnessy et al.

(10) Patent No.: US 9,488,547 B2
(45) Date of Patent: Nov. 8, 2016

(54) MODULAR SYSTEM FOR EVALUATING HELMET AND SUSPENSION MATERIALS FOR PROTECTION OF NEURAL CELLS FROM SIMULATED TRAUMA

(71) Applicants: Thomas O'Shaughnessy, Arlington, VA (US); Ryan McCulloch, Alexandria, VA (US); Amit Bagchi, Rockville, MD (US); Kirth Simmonds, Clinton, MD (US); Clark Mitchell, Woodbridge, VA (US)

(72) Inventors: Thomas O'Shaughnessy, Arlington, VA (US); Ryan McCulloch, Alexandria, VA (US); Amit Bagchi, Rockville, MD (US); Kirth Simmonds, Clinton, MD (US); Clark Mitchell, Woodbridge, VA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 241 days.

(21) Appl. No.: 14/486,622

(22) Filed: Sep. 15, 2014

(65) Prior Publication Data

US 2016/0076967 A1  Mar. 17, 2016

(51) Int. Cl.
*G01N 3/30* (2006.01)
*G01M 7/08* (2006.01)
*G01N 3/303* (2006.01)
*G01L 5/00* (2006.01)

(52) U.S. Cl.
CPC .............. *G01M 7/08* (2013.01); *G01L 5/0052* (2013.01); *G01N 3/303* (2013.01)

(58) Field of Classification Search
CPC ....... G01M 7/08; G01L 5/0052; G01N 3/30; G01N 3/303

USPC ................... 73/11.04, 12.01, 12.06
See application file for complete search history.

(56) References Cited

U.S. PATENT DOCUMENTS

| | | | |
|---|---|---|---|
| 8,725,449 B2 | 5/2014 | Roberts et al. | |
| 2005/0100873 A1* | 5/2005 | Meythaler | G09B 23/30 434/267 |
| 2008/0256685 A1* | 10/2008 | Lampe | A42B 3/068 2/411 |
| 2010/0311025 A1* | 12/2010 | Everett | C08L 89/04 434/262 |
| 2013/0055790 A1* | 3/2013 | Bhatnagar | G01N 3/313 73/12.11 |
| 2015/0080766 A1* | 3/2015 | Ji | A61B 5/11 600/595 |

OTHER PUBLICATIONS

Brozoski FT, McEntire BJ, Crowley JS, Padgett KL: Enhancing Injury Protection Capabilities of Army Combat Helmets. 2006.
Reneer et al., "A Multi-Mode Shock Tube for Investigation of Blast-Induced Traumatic Brain Injury" J. Neurotrauma 28:95-104 (Jan. 2011).
Arun P, Spadaro J, John J, Gharavi RB, Bentley TB, Nambiar MP. (2011) "Studies on blast traumatic brain injury using in-vitro model with shock tube." Neuroreport 22: 379-384.
Effgen GW, Hue CD, Vogel III E, Panzer MB, Meaney DF, Bass CR, Morrison III B. (2012) "A multiscale approach to blast neurotrauma modeling: part II: methodology for inducing blast injury to in vitro models." Frontiers in Neurology 3: 1-10.

* cited by examiner

*Primary Examiner* — Benjamin Schmitt
(74) *Attorney, Agent, or Firm* — US Naval Research Laboratory; Roy Roberts

(57) ABSTRACT

A modular system is designed to interface cell cultures to a shock tube (simulated blast) and/or drop tower (simulated blunt impact) for testing of helmet and helmet pad materials for mitigating cell injury. It includes a set of layers including helmet material, optionally helmet pad, simulated skin, simulated skull, and simulated bulk brain tissue.

11 Claims, 15 Drawing Sheets

MODULAR SYSTEM FOR EVALUATING HELMET AND SUSPENSION MATERIALS FOR PROTECTION OF NEURAL CELLS FROM SIMULATED TRAUMA

BACKGROUND

Current helmet testing is designed to assess resistance to ballistic impacts from small arms and fragments, and is conducted on metallic head forms covered with a layer of clay. Performance criteria for the helmet is on a pass/fail basis determined on lack of penetration of the helmet and a deformation of the clay layer that does not exceed a specified depth. Blunt trauma testing is done using a drop tower, again with simple criteria and metallic head forms. No standardized method exists for evaluating helmets for mitigating blast-induced mild traumatic brain injury. A need exists for improved techniques for evaluating helmet materials for protection against trauma.

BRIEF SUMMARY

In one embodiment, a system for testing helmet materials includes a layer of helmet material, a layer of skin/skull simulant, a layer of a first brain matter simulant, and a fitting adapted to hold a cell culture, these elements stacked together in the above-listed sequence as a modular assembly.

Another embodiment includes subjecting the system of the above embodiment to a physical insult such as a drop or pressure wave, then measuring a result of the physical insult.

BRIEF DESCRIPTION OF THE DRAWINGS

FIG. 1A shows an assembled system held together by four bolts with a mounting bracket for attachment to a standard DOT HYBRID III neck (not shown). FIG. 1B is an exploded view of the assembly of FIG. 1 without the bolts and plastic retainers, showing the layers simulating the head, including helmet material, helmet pad, simulants of skin, skull, and brain, and a neuronal cell culture on a base plate. The cell culture may optionally be in a holder for a standard 35 mm culture dish, or a microelectrode array chamber, or a 3D cell pack, preferably sandwiched in contact between two brain matter simulants. FIG. 1C shows the use of a holder for a conventional 35 mm dish, while FIG. 1D shows the use of a microelectrode array chamber. Either sort of cell culture may be sandwiched between two layers of brain matter simulant.

FIG. 4A shows an example of pressure tuning by distance. This graph shows the peak pressure measure in a 35 mm dish chamber at various distances from the shock tube given a fixed output pressure from the shock tube. FIG. 4B shows the same data for peak acceleration. Inset is the acceleration waveform recorded from a shock tube exposure. FIG. 4C shows that negligible strain is present at the maximum output of the shock tube and a minimum distance of 4 inches.

FIG. 6A shows the clamp section with underlying helmet and pad layers. FIG. 6B shows the system mounted to the drop tower.

FIG. 10A shows electrical recordings from cortex neurons before and after exposure to a simulated blast wave. The left panel is a control (no blast wave, just mounted on the shock tube) and the right panel is a cell culture exposed to a shock wave. After exposure, it was found the rate of action potential generation by the neurons was significantly increased and much more variable than prior to exposure.

DETAILED DESCRIPTION

Definitions

Figure 1B:
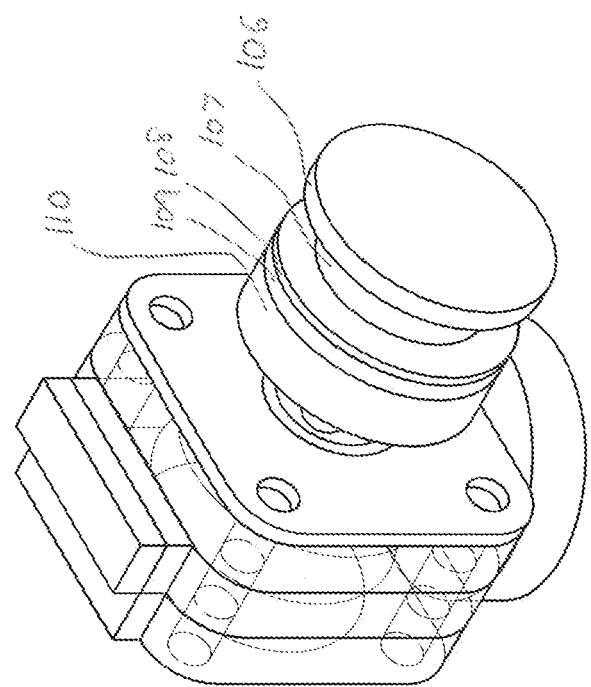
FIGS. 1A-D show exemplary assemblies for evaluating helmet and suspension materials.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

The term "skin/skull simulant" refers to a combination of materials having mechanical properties similar to that of human skin and skull, and suitable for evaluation of helmet materials as described herein.

The term "brain matter simulant" refers to a material having mechanical properties similar to that of human brain matter and suitable for evaluation of helmet materials as described herein.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

Overview

Conventional types of testing of helmet materials do not take into account the effects of a blast wave and certainly do not look at the effects of the blast wave at the level of the cells within the brain. Cellular level effects are important as mild-to-moderate traumatic brain injury (TBI) is thought to be due to damage at the level of the cell and it often occurs in the absence of visible physical trauma on modern imaging systems.

At the US Naval Research Laboratory (NRL), instrumented surrogate model headforms made of compliant skull and polymeric materials, which emulate brain biomechanical properties, have been able to provide pressure and acceleration data for blast and ballistic loading with and without a helmet. However, such systems provide purely mechanical data which are not directly linked with neural cell injuries, except through correlations with data from live animals subjected to similar blast and ballistic loadings.

While the present standard for helmet testing does not take into account blast wave effects, there are systems that are being used to gather this type of data. A primary example of this is the NRL's own GelMan-Head surrogate that places accelerometers and pressure sensors within and around a gel-based brain, skull, tissue model of the human head in order to measure the forces resulting in key locations in response to real and simulated blast waves. Helmet systems placed on the GelMan surrogate are tested to determine their ability to reduce these measured forces. However, this model system still lacks the ability to examine cellular level effects.

Current blunt impact helmet testing utilizes a metal head form that approximates the weight and size of a human head with an accelerometer mounted at the centroid of the headform. A helmet with padding and suspension in place are affixed to a head form on a drop tower. Subsequently, drops to a solid anvil are conducted from pre-determined heights. Performance criteria for the helmet is pass/fail based on acceleration of the head form centroid not exceeding a threshold value. The impacts are conducted to achieve standard velocities of 10.0, 14.1, or 17.3 feet per second (fps) at impact (Brozoski, 2006).

Described herein is a modular system for testing helmet and optionally helmet padding and/or suspension materials for their ability to protect live neurons from the effects of simulated blast waves or blunt impacts. The apparatus includes parts to secure neuronal cultures, in a variety of formats, behind layers of helmet material, suspension padding, and simulated skin, skull, and brain layers. The apparatus may be mounted in front of a shock tube for blast testing or on a drop tower for blunt impact experiments. After the simulated trauma, the neuronal cells' function and viability are assessed to determine if the helmet materials were able to mitigate damage to the cells.

This system is designed to interface cell cultures to either a shock tube (simulated blast) or drop tower (simulated blunt impact) for testing of helmet and helmet pad materials for mitigating cell injury. Key to this system is the set of layers: helmet material, pad, simulated skin, simulated skull, and simulated bulk brain tissue. The cells sit behind or within, depending on configuration, the simulated brain tissue in one of a number of cassette style chambers which allow for a variety of testing to be performed. The cell "cassettes" can be rapidly inserted and removed for testing of multiple cultures in a short time. Similarly, fresh helmet material and pads can be quickly swapped in for rapid testing.

Blast Testing Configuration

The system includes a number of pieces that can be assembled into a variety of configurations to hold 2D or 3D cell cultures in front of a shock tube for testing. The pieces may be made of suitable material such as plastic and/or aluminum. The assembled system is then placed in operational contact with a shock tube, either mounted directly to the shock tube or used in a standoff configuration while mounted to, for example, a standard DOT HYBRID III neck. This configuration is shown in FIGS. 1 and 2. Aspects of an assembly used for blast testing may also be used for blunt impact testing.

Figure 1A:
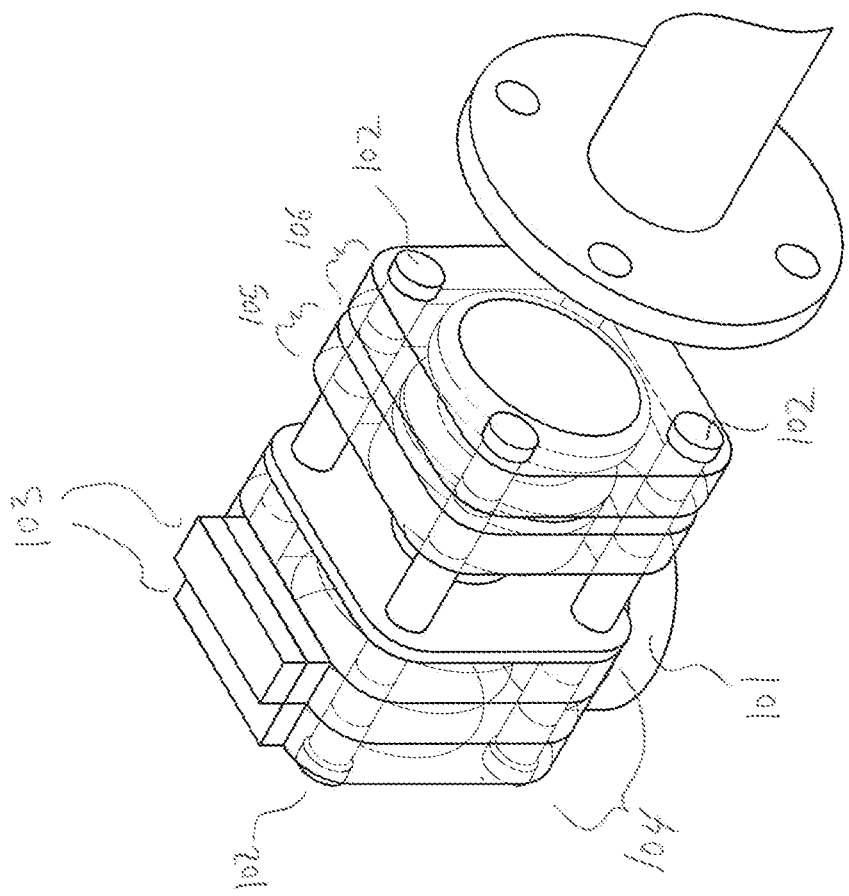
Figure 1D:
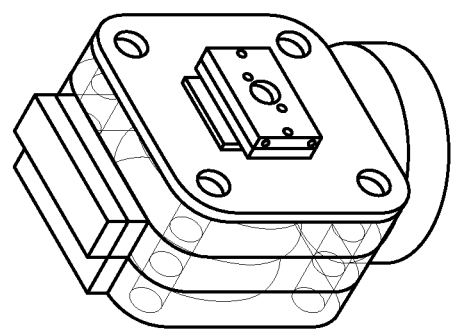
Figure 1C:
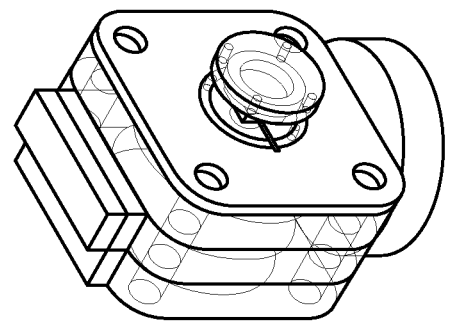
Figure 2:
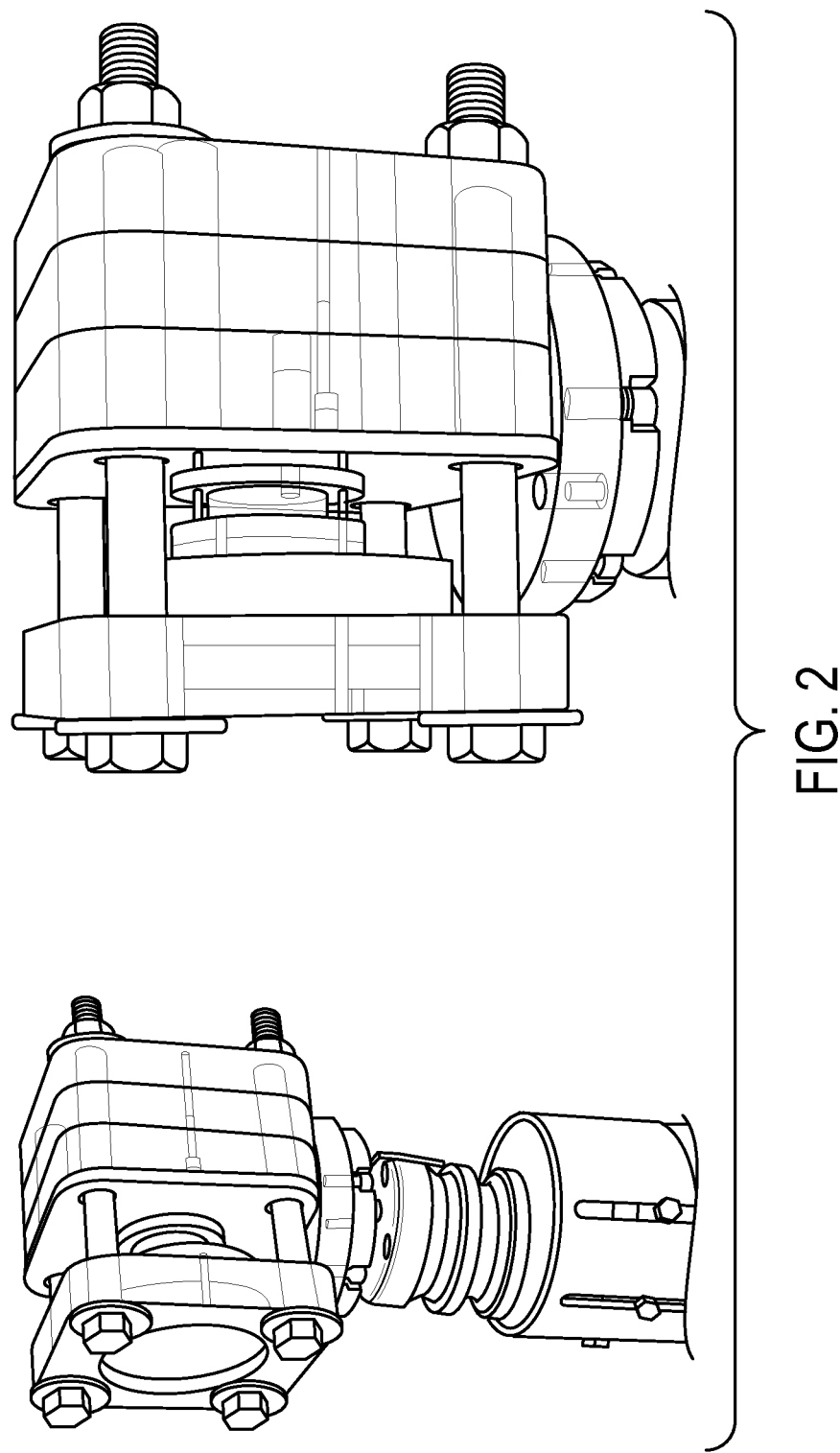
FIG. 2 the system in standoff configuration, without a helmet layer and utilizing a 35 mm dish holder for the cell culture. The left image shows the positioning of the system relative to the end of the shock tube (left side of image; blue) and mounted on a DOT HYBRID III neck, while the right image gives a better view of the layers.

FIG. 1A shows an exemplary assembly held together by four bolts (102) with a mounting bracket 101 for attachment to a standard DOT HYBRID III neck (not shown). Acceleration tuning weights 103 may be particularly useful when doing blunt impact testing. A fitting or base plate adapted to hold a cell culture 104, for example, a conventional 35 mm dish or alternatives discussed below. Also illustrated are a skin/skull/tissue holder 105 suitable for holding skin/skull simulant and brain matter simulant, and a holder 106 for helmet material and optionally helmet pad material. FIG. 1B is an exploded view of the assembly of FIG. 1 without the bolts and retainers, showing the layers simulating the head, including helmet material 106, helmet pad material 107, simulants of skin 108, skull 109, and brain 110.

Figure 3:
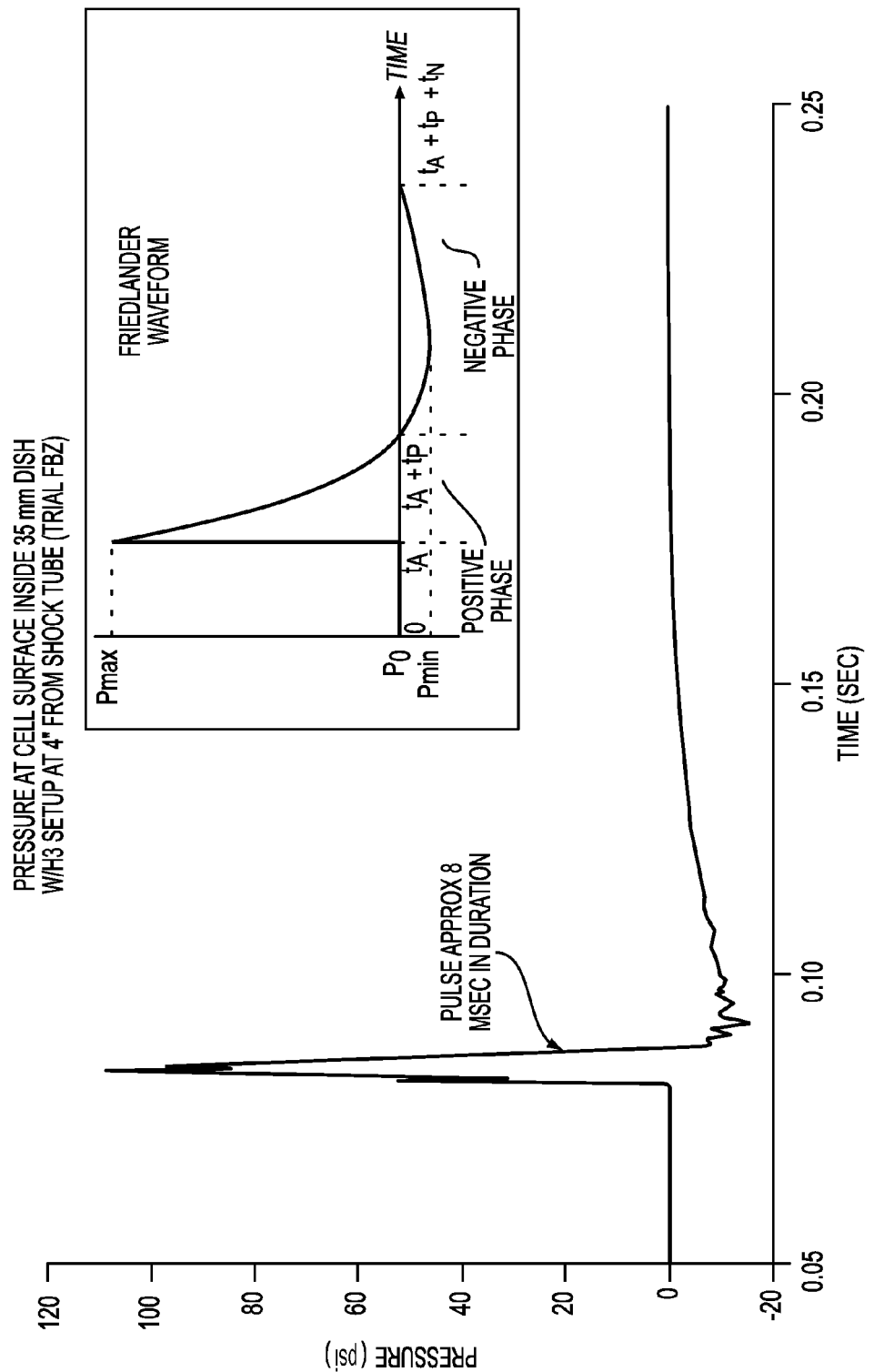
FIG. 3 shows an example of a pressure waveform recorded in the 35 mm dish chamber. The inset is the classic Friedlander waveform, the idealized blast pressure waveform.

Control and isolation of the forces generated by the shock tube are important design considerations of this system, allowing for complex examination of how the simulated blast wave is impacting the cells. The four key parameters in the coupled shock wave are rise time of the leading edge, peak pressure, velocity, and pulse width (or loading duration). The resultants of these within the cell cultures are pressure differentials, acceleration, and strain. The system generates a pressure waveform inside the cell culture chamber that closely matches the idealized blast pressure waveform (FIG. 3), known as the Friedlander wave.

Figures 4A, 4B:
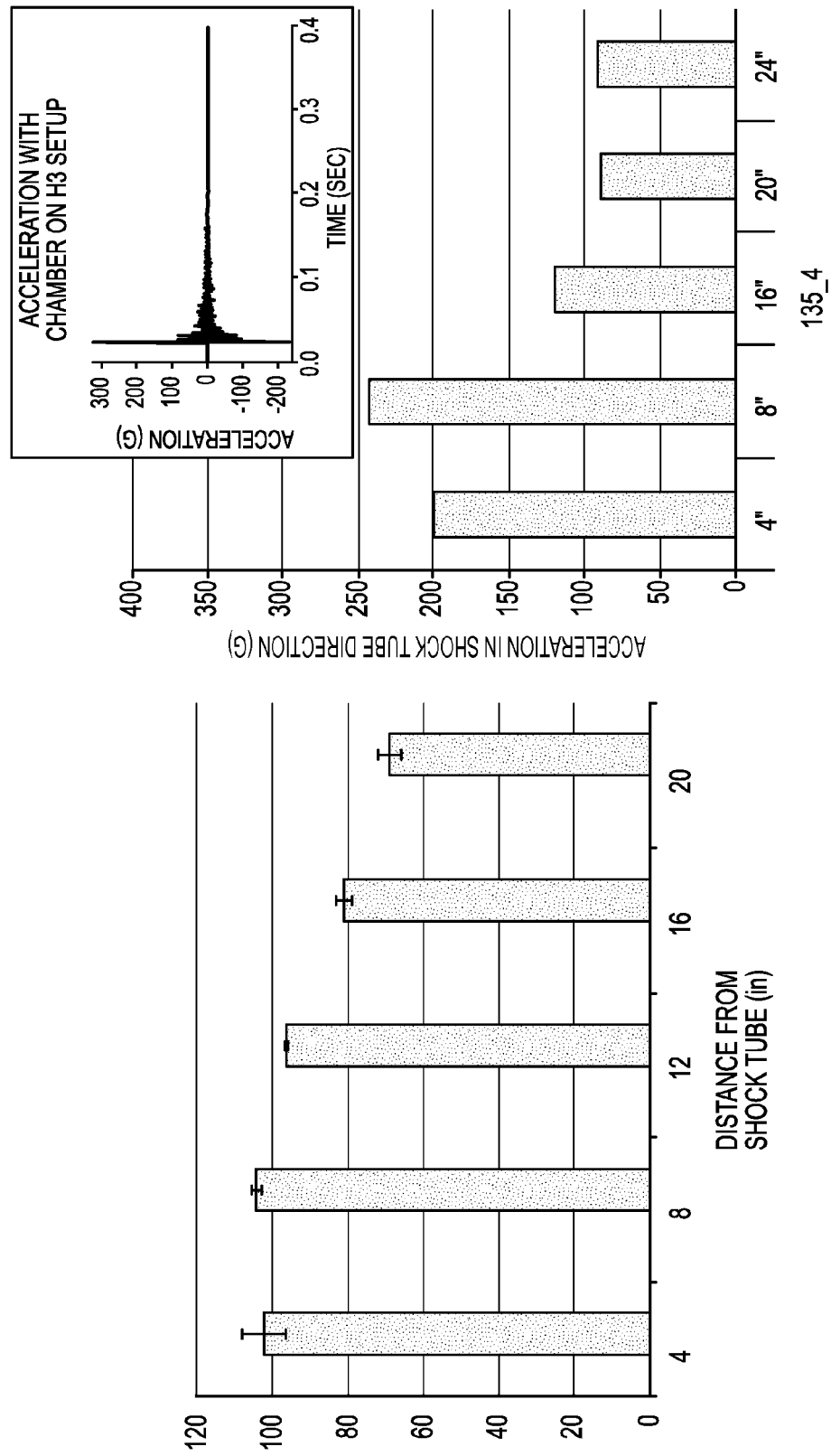
FIGS. 4A-4C show results with various distances from a shock tube.
Figure 4C:
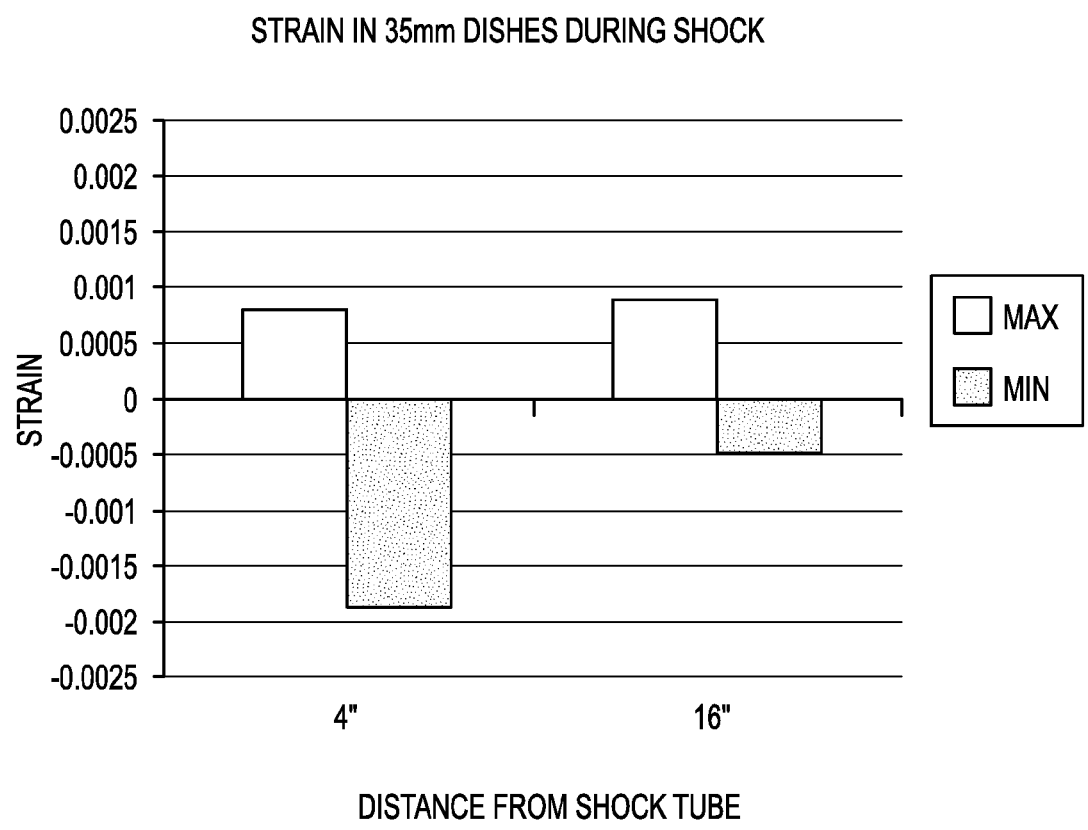

Tuning of the pressure profile can be achieved by a combination of changing the pressure output of the shock tube and the distance of the cell culture from the end of the shock tube. These parameters will also adjust the acceleration experienced by the cell culture (FIG. 4). Acceleration of the system can be tuned independently from pressure by adjusting the amount of weight placed on the back of the assembled system (see FIG. 1A.) For cultures on 2D surfaces (35 mm dishes or microelectrode arrays), the strains induced by the system are negligible (FIG. 4). Forces were measured by placing commercial sensors into a cell chamber without cells and making repeated measures to ensure reproducibility.

In order to test helmet/pad materials, a series of layers were mounted in front of the chosen cell cartridge configuration (FIG. 1). These layers included the helmet material to be tested as well as a helmet suspension pad (if desired), followed by a commercially available skin/skull simulant (Synbone AG, Switzerland), and finally a layer simulating brain matter made from 50% SIM-TEST ballistic gel (Corbin, Oreg.) and/or Sylgard 184 (Dow Corning, USA). Other simulants can be used. The system can be operated in the absence of the helmet layers as a control. The cell cultures are placed behind the helmet/head layers using one of a number of configurations depending on what biological parameters are being examined. For electrical recordings from microelectrode arrays (MEA), the system accepts the previously designed NRL MEA cartridge developed as part of the neuron-based biosensor program. Culture packs containing 3D cell cultures in a collagen gel can be sandwiched between two layers of brain tissue simulant, with a fitting adapted to hold a cell culture between the layers.

Other suitable layers can be used other than those described above, including modifications to those skilled in the art. For example, the layer of skin/skull simulant could be made up of two distinct items combined in the system, rather than the single commercial simulant used in the example.

This system offers several advantages. First, its modular nature allows it to be adapted to a wide range of shock tubes, cell cultures, and chambers. Second, the multi-layered structure of the system (helmet, pad, skin, skull, brain) allow for testing of helmet materials for mitigating damage to neural cells from blast wave damage by simulating the materials the blast wave would need to penetrate to reach the cells in a human head. Furthermore, the ability to tune and/or isolate the forces of the shock wave (pressure, acceleration, strain) allows for fine control over the exposure of the cells to simulated blast waves.

Blunt Impact Testing Configuration

In this configuration, the system consists of a number of pieces that can be assembled to hold two-dimensional (2D) or three-dimensional (3D) cell cultures in a layered stack for blunt impact testing, such as from a drop tower. Optionally, this configuration may include many if not all of the same layers as used for blast testing. The pieces may be made of suitable material such as plastic and/or aluminum. The assembled system is preferably configured to allow mounting directly to the drop tower. The testing described herein employed a Helmet Impact Tower (Biokinetics, Ottawa Canada). This configuration is shown in FIGS. 5 and 6.

This configuration may be designed to match the weight of a standard drop tower head form (5.0 kg) so that results are comparable to accepted testing scenarios. The standard head form is metal and is used to evaluate for differences in helmet material and suspension in terms of peak accelerations. The system described here supplements the standard test goals, with the addition of a simulated brain layer with a void that can accommodate a cell culture chamber. Additionally, a microelectrode array cartridge can be affixed to the test system to monitor changes in electrical activity.

Figure 5:
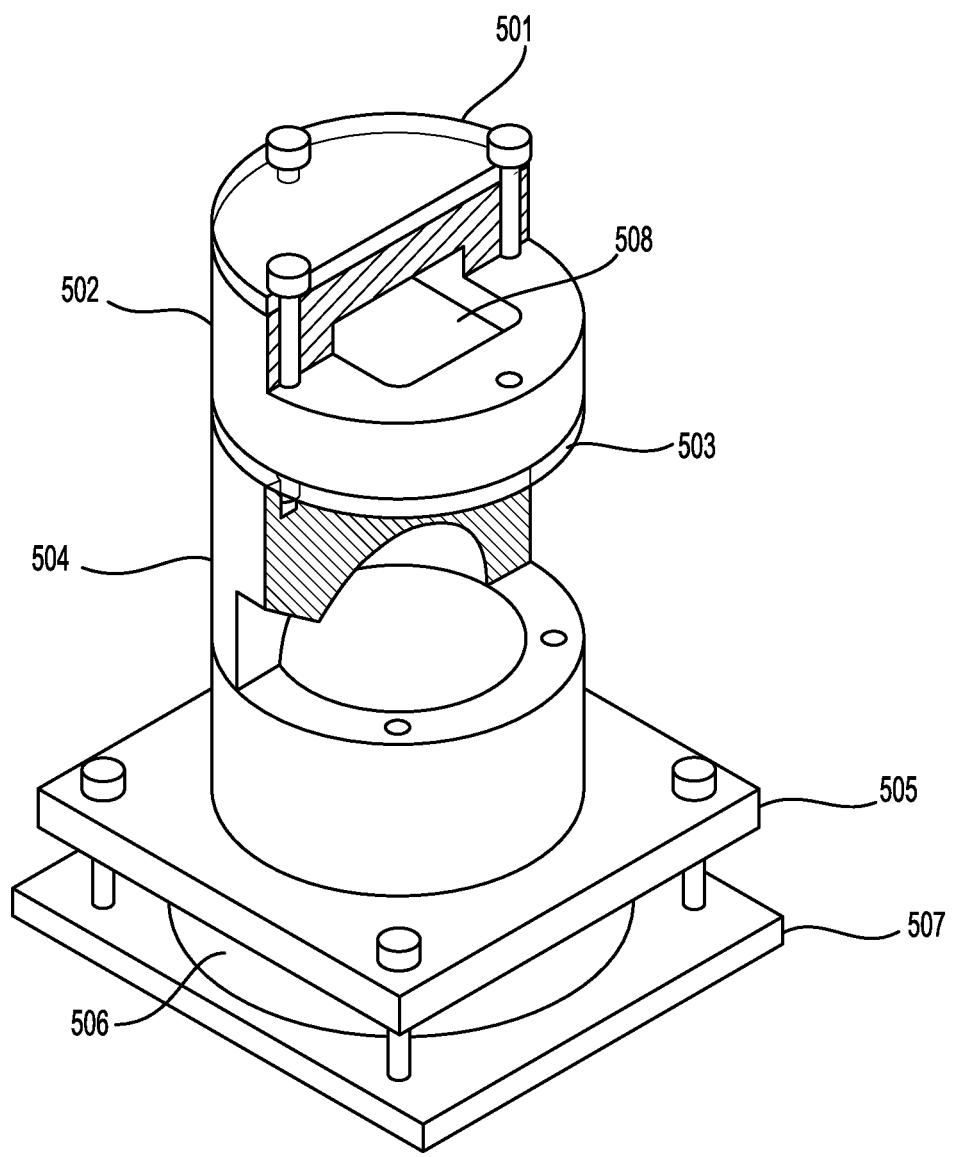
FIG. 5 shows an exemplary system configured for drop tower testing.
Figure 6A:
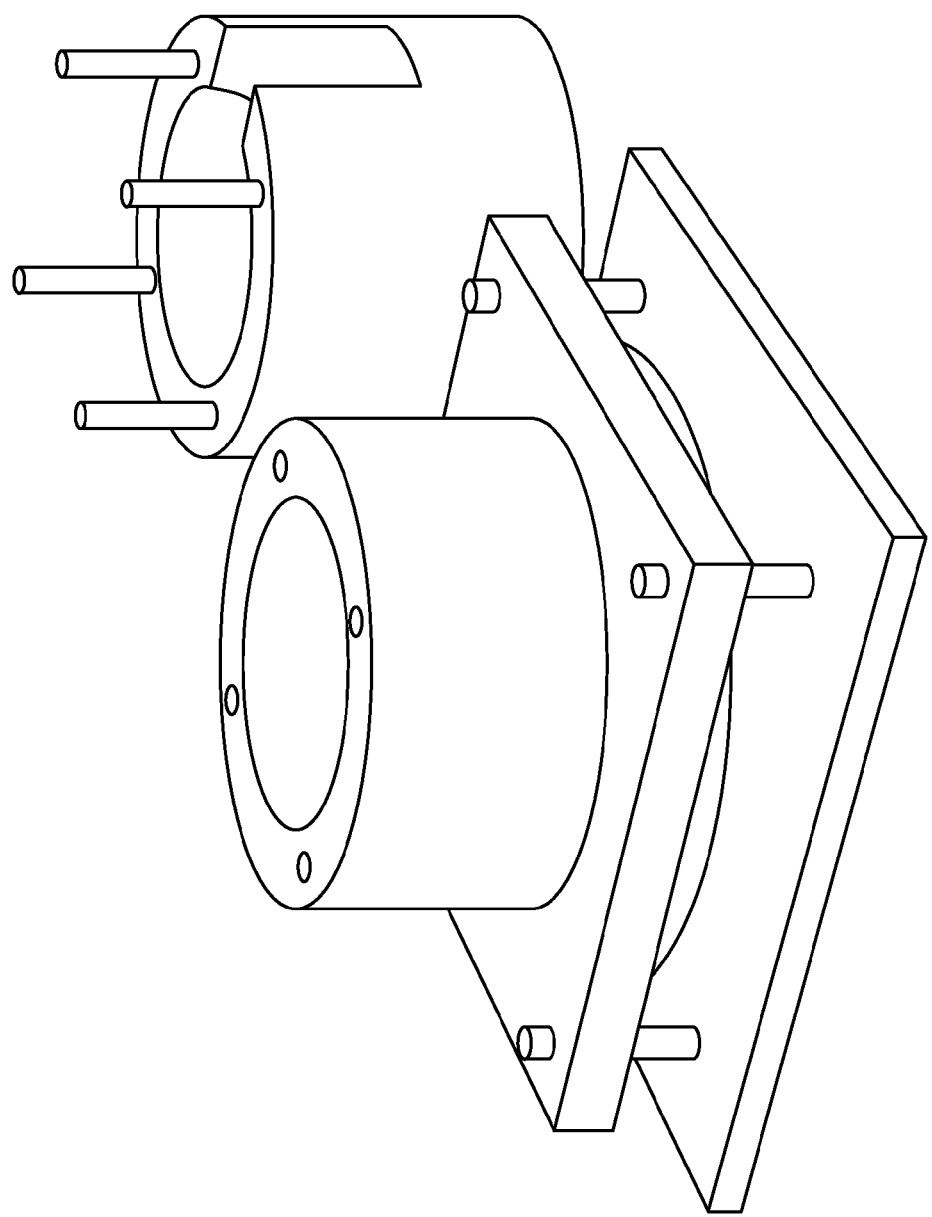
FIGS. 6A and 6B show the modular system.
Figure 6B:
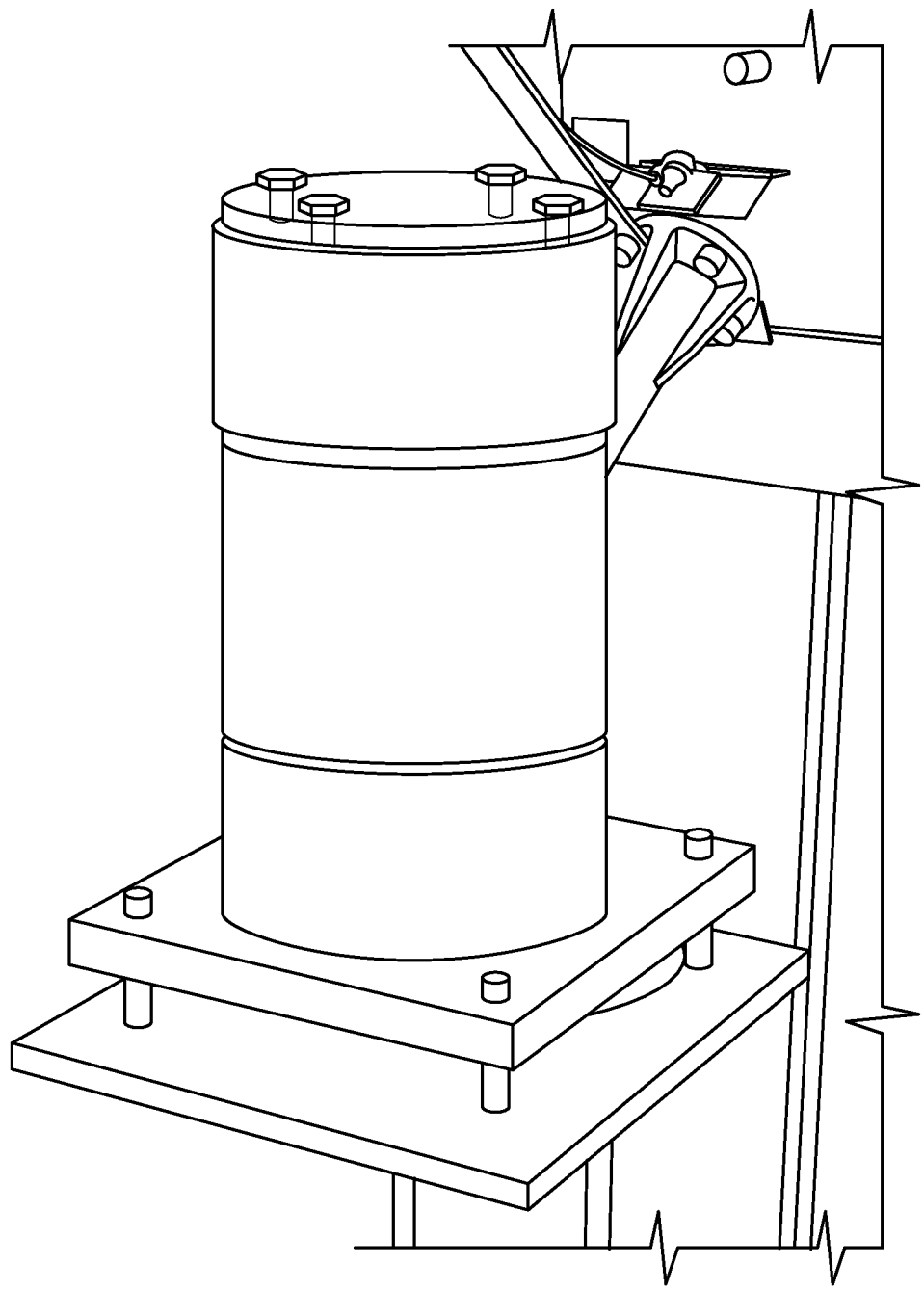

An exemplary system is now described as illustrated in FIGS. 5, 6A, and 6B. It includes a top retention plate 501, top and bottom gel brain layers 502, bottom retention plate 503, top and bottom drop tower adaptor clamp 504, helmet mount plate 505, helmet pad 506, helmet plate 507. The system is held together with bolts. The cell culture may be housed in a 2D or 3D NRL cell pack (not shown) sandwiched between the two layers of simulated brain material in a matched pocket (3D version shown). The top includes a brain simulant layer 502 that is manufactured as two halves.

The simulant can be made from a 50% collagen gel (SIM_TEST, Corbin, Oreg.) that simulates the modulus of brain tissue. The void 508 between the layers of brain simulant is manufactured to match the dimensions of the desired cell culture system (2D, 3D, electrode array) which contains primary neural cell cultures, thus the void 508 serves as the fitting to hold the cell culture. The gel layer is sandwiched between two plastic plates 501, 503 that are attached via bolts to a drop tower adaptor clamp 504. The clamp 504 includes of a spherical void configured to clamp to a spherical end of a conventional drop tower support arm. The two halves of the clamp pieces are secured with tightened bolts. The clamp may be modified to work with other styles of drop tower.

Beneath the clamp is the helmet mount plate 505. This is a square piece that allows for attaching a flat section of helmet material 507 via four corner bolts with a helmet suspension pad 506 positioned between the helmet mount plate and the helmet material. The system is connected to the drop tower and allowed to free-fall from different heights to match the standard testing velocities for blunt impact testing. The system may also be dropped from the appropriate height to obtain a desired test velocity.

Figure 7:
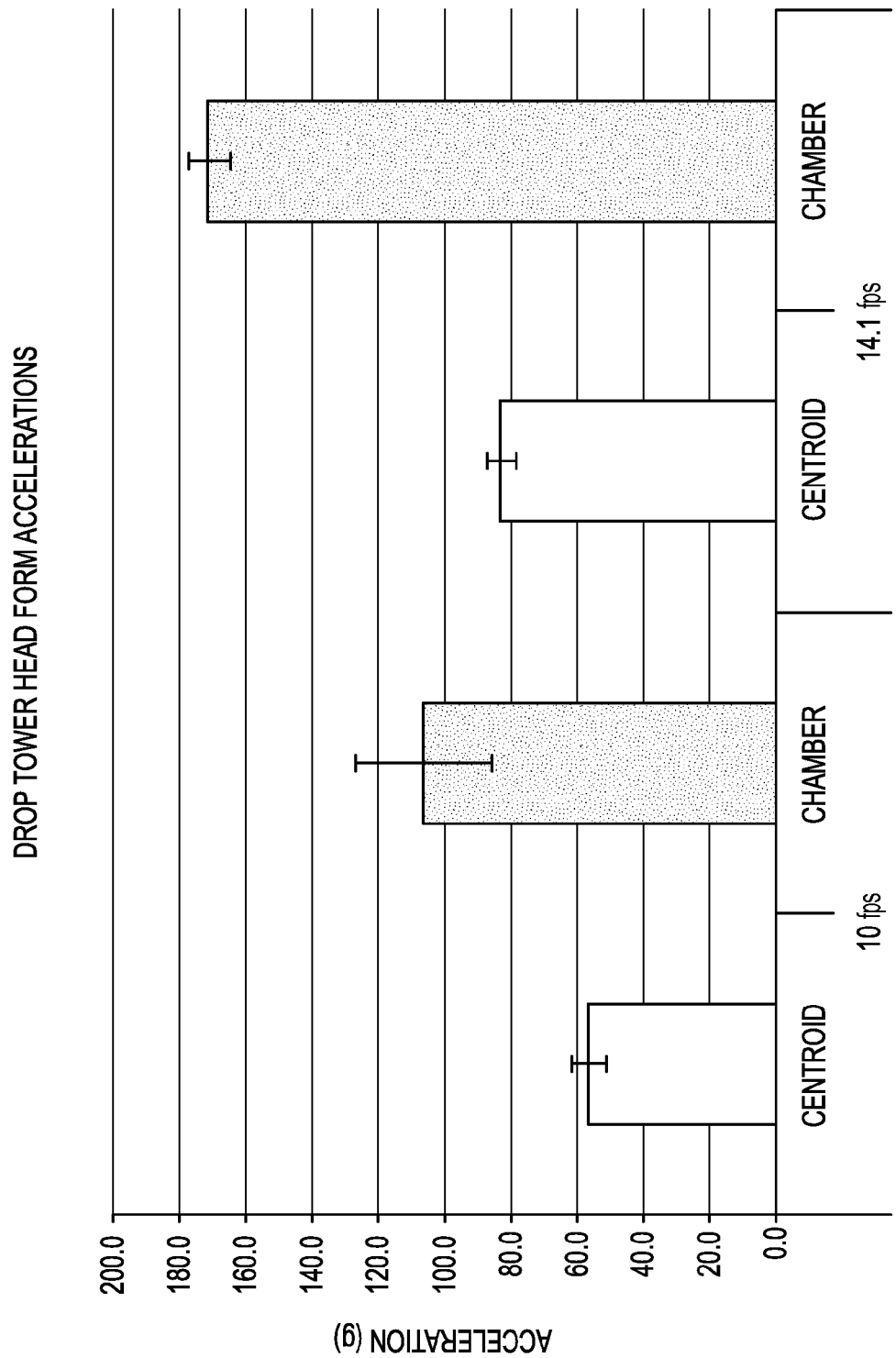
FIG. 7 shows peak accelerations in head form centroid and chamber surface during blunt impact with drop velocities of 10 fps and 14.1 fps. Bars show standard deviations of measurements

The operation of the drop tower allows for generating different accelerations by dropping the head form from different initial heights. The differing heights achieve different velocities, which result in different acceleration levels when the head form strikes the anvil. Two commonly used test velocities used for testing of protective helmets are 10.0 fps, and 14.1 fps (SMART-TE protocol, MCSC PM-ICE). Initial testing of the modular system was done at these two velocity levels, and recordings were made of the acceleration levels, both from an accelerometer mounted in the centroid of a head form and an accelerometer imbedded in the cell pack (FIG. 7).

The accelerations measured by the centroid mounted accelerometer are similar for the head form and this layered stack system. At 10 fps velocity, a drop to the crown of the head form results in an acceleration of 68.6 g (1.2 g) (this and subsequent values are presented as mean followed by standard deviation in parentheses) and an acceleration of 56.3 g (5.2 g) for the layered stack. At 14.1 fps, a drop to the crown of the head form results in an acceleration of 106.1 g (3.1 g), and an acceleration of 82.9 g (4.4 g) at the centroid for the layered stack.

This system allows for studying the effect of impact on cells, can incorporate multiple types of cell chambers, and can evaluate the effect of impact velocity on cellular response. It can also be used for evaluating helmet materials, suspension materials, or combinations of the two in order to assess relative increases or decreases in afforded protection. The testing device incorporates aspects of standardized military testing of helmet and suspension systems.

Cell Culture and Measurements

The cell culture under test can be one or more sealed cell packs, for example those grown in three-dimensional culture, and/or conventionally grown cells such as those grown in 35 mm culture dishes.

In a preferred embodiment, the cell culture is a primary neural cell culture, for example murine neural cell culture.

Exemplary suitable sealed cell packs are described in commonly-owned U.S. patent application Ser. No. 14/197,724 filed on Mar. 5, 2014, incorporated herein by reference. The cultures can be sealed at the time of culture to maintain sterility, thus allowing the cells to be removed from a cell culture laboratory for testing in a multitude of scenarios and environmental conditions, but the cell packs feature gas-permeable membranes to allow for exchange of oxygen and carbon dioxide to maintain viability of the cells. Such cell packs preferably allow for a three-dimensional cell culture that better mimics the in vivo cellular environment under in vitro conditions as compared to traditional growth in a monolayer. Furthermore, such a cell pack allows for the passage of mechanical forces (pressure, force, acceleration, strain, etc.) into the culture chamber via a flexible membrane.

Figure 8:
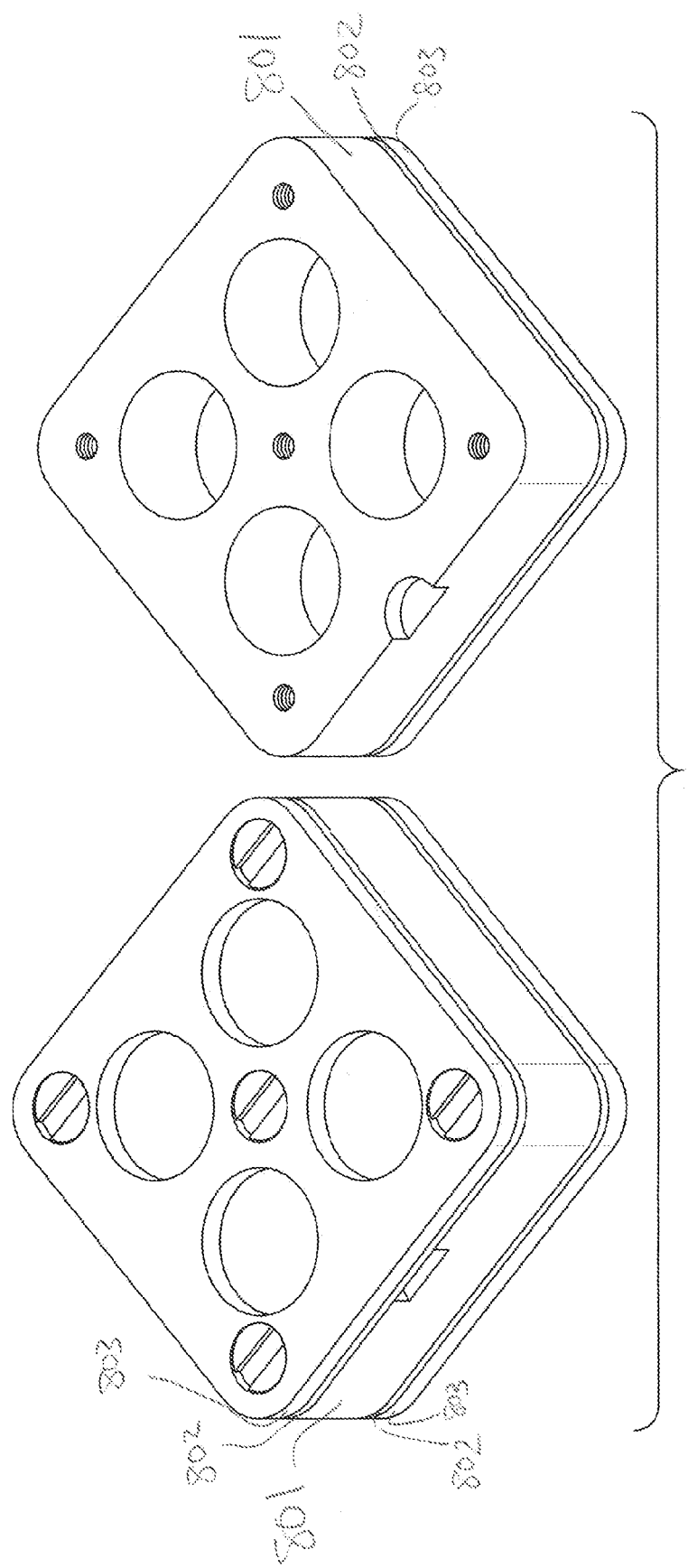
FIG. 8 shows an exemplary 3D cell pack shown fully assembled (left) and with the top seal removed (right).

An exemplary 3D culture chamber was constructed of polysulfone. The dimensions of the chamber were 2 in×2 in×0.65 in. There are 4 culture chambers in each within each well having a diameter of 0.5 in. The tops and bottoms of each chamber are tapped for 5 screws (6-32 thread). A bottom layer of 1/32 in clear silicone rubber is positioned against the polysulfone. Another aluminum layer (1/8 in thick) is positioned against the rubber and 5 screws are put in place to hold this bottom layer on the chamber (FIG. 8). The polysulfone body 801, the silicone rubber 802, and the gray material is aluminum. The aluminum base layer has 4 holes matching the culture chambers. This allows for passage of a pressure wave directly through the silicone layer and into the culture chamber. Furthermore, the exposed silicone beneath the cell culture allows for passage/exchange of both $CO_2$ and $O_2$ to maintain the viability of the cells in culture. However the silicone rubber layer stops the passage of bacteria and thus maintains the sterility of the culture. The chambers are filled with a collagen hydrogel with suspended primary culture neural cells. The collagen is allowed to "gel" on the bottom surface of the chamber (the silicone layer) and the rest of the chamber is filled with culture media. A silicone gasket (essentially the same as the bottom one) is placed on the top of the chamber, and then a final top aluminum plate is put in place. This may be either a solid plate or have holes matching the chambers, depending on the testing set-up. The top layers are then affixed with 5 screws. The entire chamber may then be placed in an incubator to maintain temperature and proper $CO_2$ saturation. The chamber may be removed at any point for testing as sterility is maintained in the chamber wells via the top and bottom silicone layers.

The system may be sterilized by placing all of the components in an autoclave. Alternately, UV exposure or a 70% ethanol mixture can be used. The silicone may be substituted with a thin polystyrene film to allow imaging through the layer. The size of the wells themselves may be varied to allow for smaller or larger culture sizes.

Figure 9:
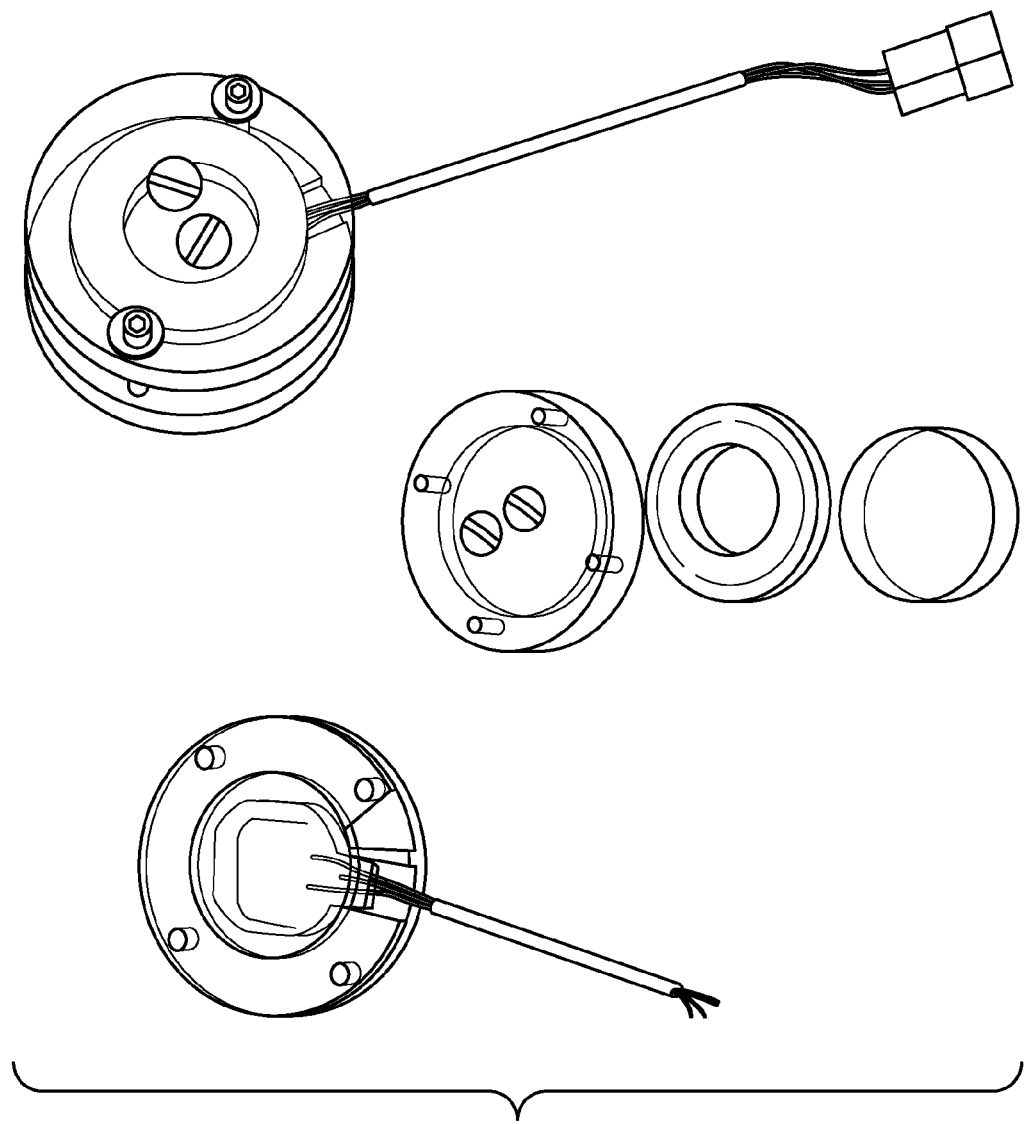
FIG. 9 shows an assembled 35 mm dish holder at the top of the image. The middle inset shows (from left to right) the top with two fill ports, the gasket, and a standard 35 mm dish. The lower image is of the bottom plate of the holder showing the incorporated resistive heater and thermistor.

Another exemplary fitting was designed to allow the use of cell cultures grown in traditional 35 mm dishes as commonly used in cell culture (FIG. 9). The fitting included both top and bottom acrylic pieces with recesses to secure the 35 mm dish. The bottom piece contains a resistive heater and thermistor that can be attached to a commercial laboratory heating controller (Warner Instruments model#TC-344B) for maintaining cell temperature during a test. The top contains two ports for filling and sealing the assembled chamber with media. The ports can be sealed with nylon screws (shown) or fitted with standard luer connectors. A 10 durometer, quarter inch (0.25 in) thick silicon rubber gasket is fitted into the chamber top and serves to seal the chamber and allow compression of the chamber from the external pressure pulse into the cell culture media. The chambers can be sterilized with UV light (e.g., for 15 minutes) and when assembled under sterile conditions, they will keep the cell cultures sterile even when the assembled and sealed chambers are in a non-sterile environment.

Strains can be introduced in the 2D cultures by using a dish with a flexible growth surface made from a biocompatible substance such as silicon rubber. Alternately, 3D cell cultures in hydrogels will naturally deform in response to the pressure/acceleration profile and induce strain. A 3D culture may thus provide a better model.

In addition to being able to eliminate/include strain, pressure changes can be removed by replacing the thick, soft gasket in the 35 mm dish chamber with a thin, hard gasket. This means that the system can be set to produce a complete response to the blast wave, i.e. acceleration, pressure, and strain or limited to profiles with acceleration and pressure or simply acceleration only. This allows for determination of the rolls of the individual forces on effecting the cells.

While the system was tested to work with primary culture murine cortex cells, it should accommodate nearly any type of primary cell or cell line. Culture conditions can be adjusted for different cell types.

The effect of the test on the cells may be analyzed using various techniques including electrophysiology, analysis of biochemical markers, and microscopic examination. The system may optionally include one or more sensors to measure, for example, acceleration, pressure, etc.

Test Results

Figure 10A:
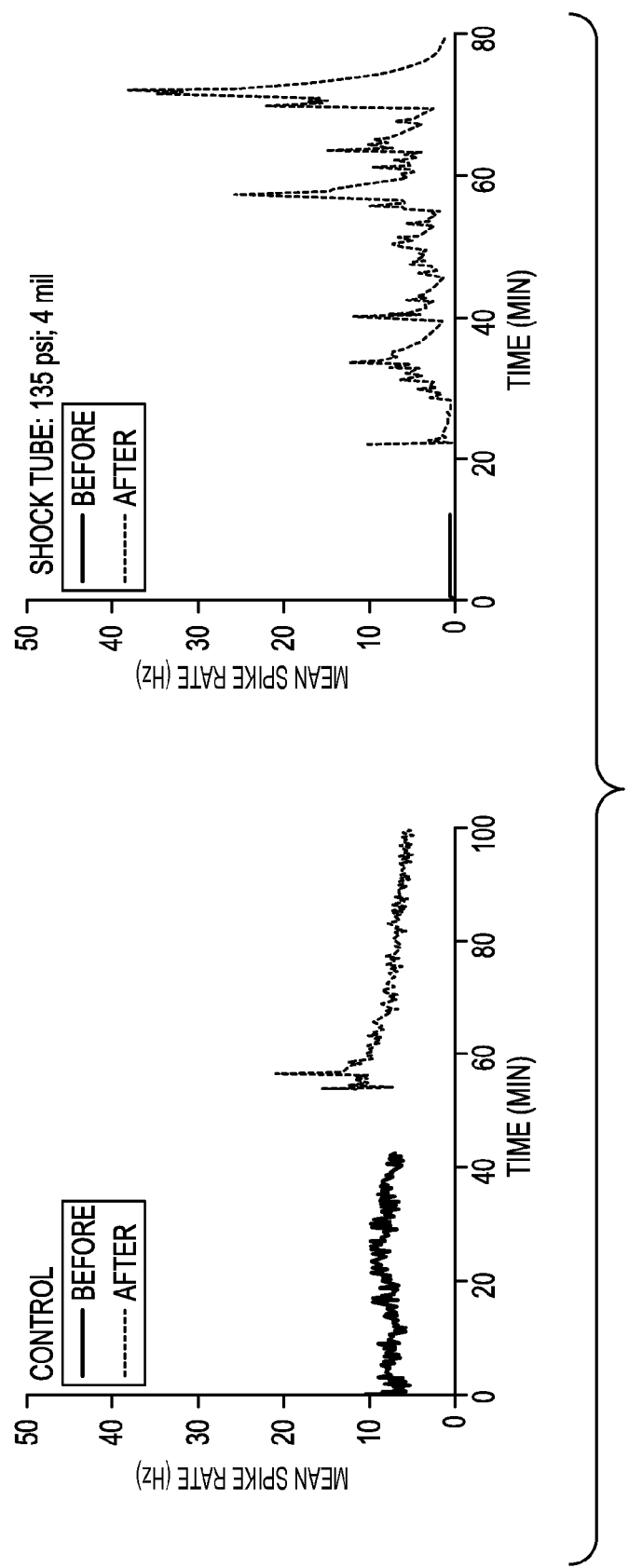
FIGS. 10A and B show results of tests on cells.

The system has been tested in a number of configurations. Initially, the system was used to examine the effect of the accelerations from a simulated shock wave on the electrical signaling (as measured by the rate of action potential generation) in the cortex cultures. These experiments were done using a configuration of the system where it was attached directly to the shock tube and the acceleration profile tuned to simulate a blast wave. The results are shown in FIG. 10A.

Figure 10B:
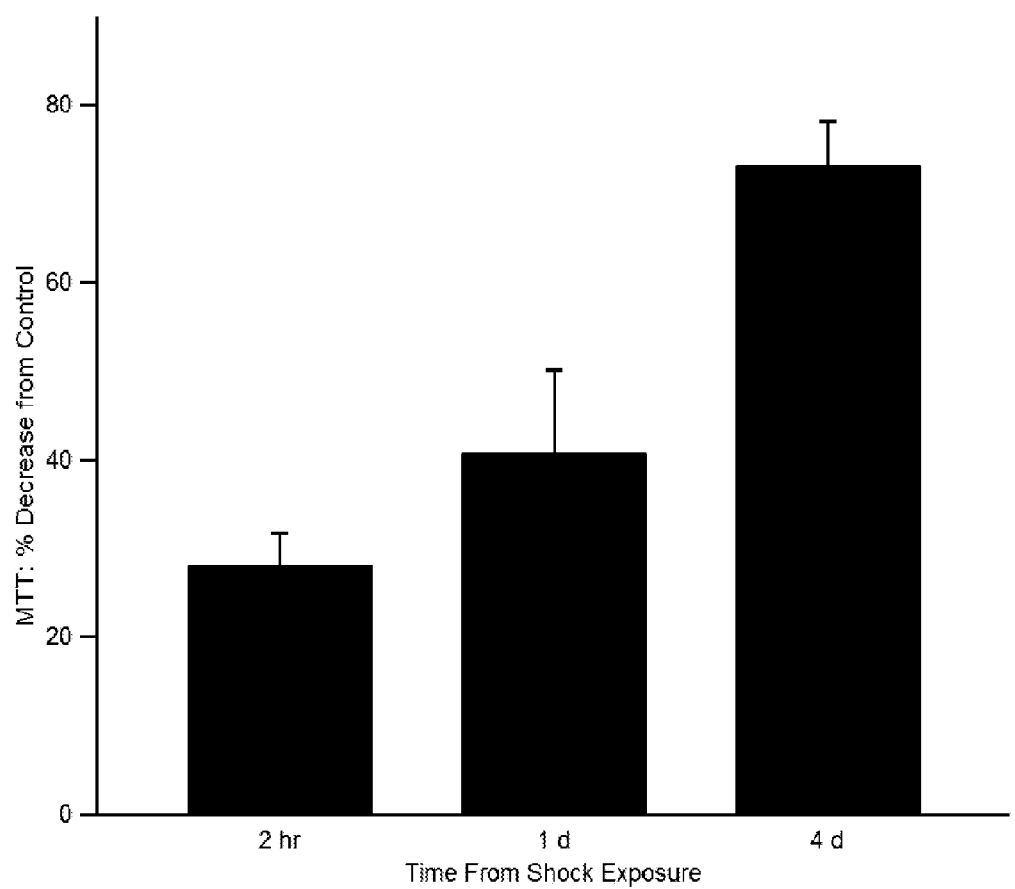
FIG. 10B shows results from an experiment in which cortex cells in a three-dimensional culture format were exposed to 33 psi shock waves (~580 g acceleration). The cell cultures were monitored for changes in metabolic activity over time using a commercial 3-(4,5-dimethylthiazol-2-yl)-2,5-diphenyltetrazolium bromide (MTT) assay. At all measured times post exposure, cell metabolism was decreased vs. control (non-exposed) cells. This effect was persistent and progressive out to four days post exposure.

A second set of experiments was performed using the 3D culture chambers and the system in the standoff configuration with just the brain layers present. Murine cortex cultures were exposed to shock waves with a peak pressure of 33 psi and peak acceleration of ~580 g. At 3 time points post shock, the metabolism of the cells was determined with a commercial assay (MTT assay, Promega). The results were compared with pair matched, unexposed cell cultures. The results are shown in FIG. 10B. The two sets of experiments demonstrated the functionality of the system for applying simulated shock waves to cell cultures with a shock tube.

Figure 11:
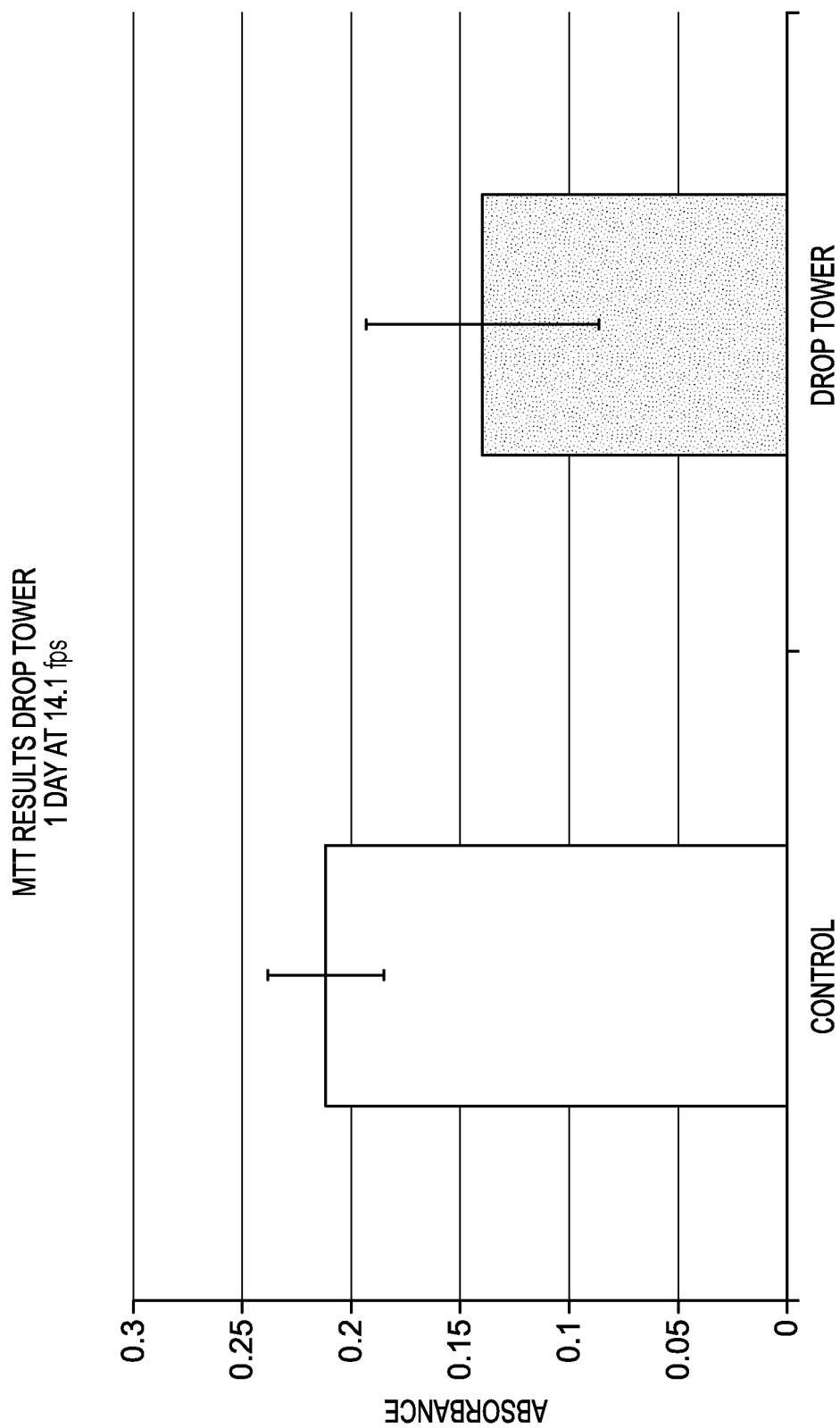
FIG. 11 shows measured absorbance for MTT assay following blunt impact of the 3D neuronal cultures. The cell cultures were dropped with the drop tower system at a velocity of 14.1 fps to generate a blunt impact. Results are compared to non-treated controls. A significant decrease in metabolic activity was observed.

The brain simulant layer can be molded/manufactured to accommodate different culture chambers. For initial testing, primary murine cortex cells were cultured in a custom cell pack within a collagen hydrogel. The cell packs were then placed in the brain simulant layer, and dropped from the appropriate height to reach a 14.1 fps velocity prior to blunt impact. This was repeated for two cell packs, each containing 4 chambers. Non-dropped cell packs were used as controls. The cultures were assessed for metabolic activity at 24 hrs post-drop with a commercial assay (MTT assay, Promega). In comparison to control, a significant decrease in metabolic activity was observed ($p=0.0045$). Results are shown in FIG. 11. The experiment demonstrates the functionality of the system for testing the exposure of neuronal cultures to a blunt impact.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

What is claimed is:

1. A system for testing helmet materials, the system comprising:
   a layer of helmet material,
   a layer of skin/skull simulant,
   a layer of a first brain matter simulant, and
   a fitting adapted to hold a cell culture,
   the above elements stacked together in the above-listed sequence as a modular assembly.

2. The system of claim 1, further comprising a helmet pad material disposed between said helmet material and said skin/skull simulant.

3. The system of claim 1, wherein said cell culture comprises living neuronal cells disposed in said fitting.

4. The system of claim 3, further comprising a microelectrode array operably connected to said cell culture.

5. The system of claim 1, having a mass of about 5.0 kilograms.

6. The system of claim 1, further comprising a second brain matter simulant, wherein said fitting is disposed between said first brain matter simulant and the second brain matter simulant.

7. The system of claim 6, further comprising a helmet pad material disposed between said helmet material and said skin/skull simulant.

8. A method of testing helmet materials, the method comprising:
   providing a modular testing system comprising
      a layer of helmet material,
      a layer of skin/skull simulant,
      a layer of a first brain matter simulant, and
      a fitting adapted to hold a cell culture,
      the above elements stacked together in the above-listed sequence as a modular assembly; and
   subjecting the modular testing system to a physical insult; and
   measuring a result of the physical insult.

9. The method of claim 8, further comprising placing said testing system in a drop tower, wherein said physical insult is an impact.

10. The method of claim 8, further comprising placing said testing system in operational contact with a shock tube, and wherein said physical insult is a pressure wave.

11. The method of claim 8, wherein said measuring comprises a measurement of electrical activity in neuronal cells.

* * * * *